United States Patent
Lin et al.

(10) Patent No.: US 12,186,753 B2
(45) Date of Patent: Jan. 7, 2025

(54) PASSIVE MIXING MICROFLUIDIC URINARY ALBUMIN CHIP (UAL-CHIP) FOR CHRONIC KIDNEY DISEASE

(71) Applicant: University of Manitoba, Winnipeg (CA)

(72) Inventors: Francis Lin, Winnipeg (CA); Jiandong Wu, Winnipeg (CA); Claudio Rigatto, Winnipeg (CA); Paul Komenda, Winnipeg (CA); Navdeep Tangri, Winnipeg (CA); Gong Zhang, Winnipeg (CA)

(73) Assignee: University of Manitoba, Winnipeg (CA)

( * ) Notice: Subject to any disclaimer, the term of this patent is extended or adjusted under 35 U.S.C. 154(b) by 814 days.

(21) Appl. No.: 17/266,217

(22) PCT Filed: Sep. 24, 2019

(86) PCT No.: PCT/CA2019/051362
§ 371 (c)(1),
(2) Date: Feb. 5, 2021

(87) PCT Pub. No.: WO2020/061690
PCT Pub. Date: Apr. 2, 2020

(65) Prior Publication Data
US 2021/0308680 A1 Oct. 7, 2021

Related U.S. Application Data

(60) Provisional application No. 62/735,295, filed on Sep. 24, 2018.

(51) Int. Cl.
*B01L 3/00* (2006.01)
*G01N 21/78* (2006.01)
(Continued)

(52) U.S. Cl.
CPC ........ *B01L 3/502776* (2013.01); *G01N 21/78* (2013.01); *G01N 33/6839* (2013.01);
(Continued)

(58) Field of Classification Search
CPC ....... B01L 3/502776; B01L 2300/0867; B01L 2300/0883; B01L 2400/0457;
(Continued)

(56) References Cited

U.S. PATENT DOCUMENTS

| 6,890,093 B2 | 5/2005 | Karp et al. |
| 7,223,363 B2 | 5/2007 | McNeely et al. |
| 2004/0132200 A1* | 7/2004 | Albarella ................. C12Q 1/28 436/108 |

(Continued)

OTHER PUBLICATIONS

Jha et al., "Chronic kidney disease: global dimension and perspectives," Lancet 382:260-272 (2013).
(Continued)

*Primary Examiner* — Jill A Warden
*Assistant Examiner* — Michael Stanley Gzybowski
(74) *Attorney, Agent, or Firm* — Dentons US LLP

(57) ABSTRACT

Described herein is a method for mixing unequal amounts of two reagents to produce a detectable reaction in a microfluidic chip. In one example, there is a fluorescent microfluidic urinary albumin chip (UAL-Chip) that exploits the nonimmunological fluorescent assay. In this chip, we constructed a passive and continuous mixing module, in which the loading process requires only an inexpensive dropper, and the signal is stable over time, as discussed below. We applied a pressure-balancing strategy based on the immiscible oil coverage which highly improves the precision in controlling the mixing ratio of sample and dye. The UAL-Chip has achieved an estimated limit of detection (LOD) of 8.4 μg/ml using albumin standards, which is below the 30 μg albumin per ml urine level considered to be indicative of kidney damage.

22 Claims, 5 Drawing Sheets

(51) Int. Cl.
*G01N 33/68* (2006.01)
*G01N 33/70* (2006.01)

(52) U.S. Cl.
CPC ...... *G01N 33/70* (2013.01); *B01L 2300/0867* (2013.01); *B01L 2300/0883* (2013.01); *B01L 2400/0457* (2013.01); *G01N 2333/76* (2013.01); *G01N 2800/347* (2013.01)

(58) Field of Classification Search
CPC .... G01N 21/78; G01N 33/6839; G01N 33/70; G01N 233/76
See application file for complete search history.

(56) References Cited

U.S. PATENT DOCUMENTS

| | | | |
|---|---|---|---|
| 2007/0062583 A1* | 3/2007 | Cox | G01N 27/44769 73/864.22 |
| 2009/0053814 A1 | 2/2009 | Patel et al. | |
| 2009/0268548 A1 | 10/2009 | Hartmann et al. | |
| 2012/0328488 A1* | 12/2012 | Puntambekar | B01L 3/5025 422/503 |

OTHER PUBLICATIONS

Tonelli et al., "Using Proteinuria and Estimated Glomerular Filtration Rate to Classify Risk in Patients With Chronic Kidney Disease," Annals of Internal Medicine 154:12-21 (2011).

Busby et al., "Comparison of Commonly Used Assays for the Detection of Microalbuminuria," The Journal of Clinical Hypertension 6(11 suppl. 3):8-12 (2004).

Du et al., "SlipChip," Lab Chip 9(16):2286-2292 (2009).

Hofmann et al., "Towards microalbuminuria determination on a disposable diagnostic microchip with integrated fluorescence detection based on thin-film organic light emitting diodes," Lab Chip 5:863-868 (2005).

Coskun et al., "Albumin testing in urine using a smart-phone," Lab Chip 13(21):4231-4238 (2013).

Yang et al., "$M_{kit}$: A cell migration assay based on microfluidic device and smartphone," Biosensors and Bioelectronics 99:259-267 (2018).

Yang et al., "Novel Developments of Mobile Sensing Based on the Integration of Microfluidic Devices and Smartphone," Lab Chip 16(6):943-958 (2016).

* cited by examiner

PASSIVE MIXING MICROFLUIDIC URINARY ALBUMIN CHIP (UAL-CHIP) FOR CHRONIC KIDNEY DISEASE

PRIOR APPLICATION INFORMATION

The instant application is a 371 of PCT Application CA2019/051362, filed Sep. 24, 2019, now abandoned, which claimed the benefit of U.S. Provisional Application Ser. No. 62/735,295, filed Sep. 24, 2018, and titled "A passive mixing microfluidic urinary albumin chip (UAL-Chip) for chronic kidney disease assessment", the entire contents of which are incorporated herein by reference for all purposes.

BACKGROUND OF THE INVENTION

Around 8-16% of the population suffer from chronic kidney disease (CKD). [1] The cause of CKD varies but some of the most common factors include diabetes, high blood pressure and cardiovascular disease. There are few signs or symptoms in the early stage of CKD, which makes early diagnosis difficult. CKD can progress to fatal end-stage kidney failure if it is not treated properly. Optimal detection and risk assessment of CKD requires simultaneous estimation of both kidney function (e.g. glomerular filtration rate [GFR]) and kidney damage (e.g. albuminuria or proteinuria). [2]

Albuminuria is a pathological condition wherein the protein albumin is abnormally presented in the urine. Thirty micrograms per millilitre (30 µg/ml) or higher of albumin in urine is considered an indicator of kidney damage. The measurement of urine albumin level is necessary for early diagnosis and monitoring of kidney disease. Urine collection is non-invasive, which makes it an ideal sample for point-of-care (POC) detection.

There are a variety of methods for assessing urinary albumin excretion, ranging from the colorimetric dipstick method to immunoassays to high-performance liquid chromatography (HPLC)-based methods. [3] While the dipstick test is inexpensive and easy to perform, its accuracy is limited. Immunoassays and HPLC methods are more accurate but suffer from complicated test procedures and require specialized facilities.

The traditional dipstick tests involve wetting a colorimetric dye-impregnated test strip with a sample of urine. The albumin concentration is determined by either visually comparing the reaction colors with the color scales on the label or reading the reaction colors with for example an analyzer. Readings are only reported in terms of negative, trace, 1+, 2+, 3+ and 4+ or the semi-quantitative values of 30, 100, 300 or 2000 mg/dL corresponding to each color change. The limit of detection (LOD) and accuracy of the dipstick tests is usually not good. For example, the Chemstrip can produce a color change only when the albumin concentration is higher than 60 µg/ml, which is 3 times higher than the recommended 20 µg/ml threshold to determine microalbuminuria. Furthermore, the emersion time of the strip in the urine and the standby time after taking it out before reading the signal are critical, raising the potential for operator errors, (e.g., color changes that occur after 2 minutes are usually of no diagnostic value). To improve the detection limit, the Micral-Test strip was developed based on an immunological reaction. In this test, urine first passes through a conjugate fleece where albumin binds to specific, gold-labeled antibodies and then flows to a detection pad. A chemical reaction in the detection pad produces a color that is compared visually to color blocks, with colors representing albumin concentrations of 0, 20, 50, and 100 µg/ml. Although the Mical-Test strip has better accuracy, the ~$10 cost per chip (vs <$1 per standard dipstick strip) makes it cost prohibitive for large-scale screening.

Traditionally, different immunologically-based laboratory methods such as immunonephelometry, immunoturbidimetry, and radioimmunoassay, have been used for the confirmation and measurement of microalbuminuria. These tests usually have higher accuracy than the dipstick strips and the radioimmunoassay was reported to have a LOD as low as 16 µg/L. However, some studies have suggested that immunological methods cannot detect all intact albumin in the urine, which raises the potential for false negative errors in detecting albuminuria. In contrast, HPLC-based laboratory tests can detect both immunoreactive and immuno-unreactive intact albumin. However, both the immunologically-based and HPLC-based laboratory tests are complicated to use and have high facility requirements. A POC method that optimally balances accuracy, cost, simplicity and low facility requirement, would be a highly desirable tool to effectively address the epidemic of CKD in poor, remote, underserviced regions of the world.

The colorimetric test for albumin typically uses bromocresol green (BCG) or bromocresol purple (BCP), which is the same dye used in the dipstick tests. It has been reported that colorimetric albumin tests based on BCG or BCP suffer from inaccuracy at low albumin concentrations.

One method that balances accuracy, cost, simplicity and facility requirement is the nonimmunological fluorescent assay, which has been reported by Kessler and colleagues. The principle of the method is based on a protein-dye complex resulting from the specific binding of a fluorescent dye to human albumin, which generates a strong fluorescent signal. Specifically, this method has higher accuracy than the dipstick method and lower cost and facility requirement than immunoassays and HPLC, suggesting it a suitable method for POC albumin detection.

The conventional method to perform the fluorescent test is to mix the reacting dye and the test sample at a fixed ratio in a well-plate; wait for several minutes for the mixture to react; and measure the fluorescent intensity from the reaction product to evaluate the albumin concentration. However, such a method requires precise solution metering equipment such as a pipette to reach the mixing ratio. In addition, the time window for detection is short, usually requiring reading of the signal within 5 minutes of the reaction starting, as after 5 minutes, the signal will change due to overreaction and evaporation, which affects the accuracy of the measurement. Furthermore, the well-plate method requires relatively large volumes of reagents (for example, tens of microliters per well).

Microfluidics enables advanced sample processing, manipulation and analysis in miniaturized fluidic devices. The low sample and reagent consumption, high-throughput, low-cost, integration and portability make microfluidics suitable for disease biomarker detection.

SUMMARY OF THE INVENTION

According to a first aspect of the invention, there is provided a method for mixing unequal amounts of two reagents to produce a detectable reaction in a microfluidic chip comprising providing a microfluidic chip comprising:
a first reagent inlet in fluid communication with a first reagent channel, said first reagent channel having a height, a width and a length, said first reagent channel having a first reagent flow rate defined by the height, the width and the length of the first reagent channel; and a second reagent inlet in fluid communication with a second reagent channel, said second reagent channel having a height, a width and a length, said second reaction channel having a second reagent flow rate defined by the height, the width and the length of the second reagent channel;

said first reagent channel and said second reagent channel meeting at a junction point, said junction point in fluid communication with a reaction channel, and said reaction channel in fluid communication with an outlet;

applying a quantity of a first reagent solution to the first reagent inlet;

applying a quantity of a second reagent solution to the second reagent inlet;

applying a quantity of oil to the first reagent inlet and the second reagent inlet, said oil having a density slightly lower than a density of the first reagent solution and a density slightly lower than a density of the second reagent solution so that said oil floats on top of the first reagent solution and the second reagent solution;

said first reagent flowing along the first reagent channel at the first reagent channel flow rate and said second reagent flowing along the second reagent channel at the second reagent channel flow rate until said first reagent and said second reagent begin mixing at the junction point, thereby producing a detectable reaction; and detecting the detectable reaction within the reaction channel.

According to another aspect of the invention, there is provided a method for detecting albumin in urine using a microfluidic chip comprising providing a microfluidic chip comprising:

a first reagent inlet in fluid communication with a first reagent channel, said first reagent channel having a height, a width and a length, said first reagent channel having a first reagent flow rate defined by the height, the width and the length of the first reagent channel;

a second reagent inlet in fluid communication with a second reagent channel, said second reagent channel having a height, a width and a length, said second reaction channel having a second reagent flow rate defined by the height, the width and the length of the second reagent channel;

said first reagent channel and said second reagent channel meeting at a junction point, said junction point in fluid communication with a reaction channel, and said reaction channel in fluid communication with an inlet;

applying a quantity of a urine to the first reagent inlet;

applying a quantity of albumin-detecting dye to the second reagent inlet;

applying a quantity of oil to the first reagent inlet and the second reagent inlet, said oil having a density slightly lower than a density of the first reagent solution and a density slightly lower than a density of the second reagent solution so that said oil floats on top of the urine and the albumin detecting reagent;

said urine flowing along the first reagent channel at the first reagent channel flow rate and said second reagent flowing along the second reagent channel at the second reagent channel flow rate until said first reagent and said second reagent begin mixing at the junction point, thereby producing a detectable reaction, wherein said first reagent channel flow rate is approximately one sixth of the flow rate of the second reagent channel; and detecting the detectable reaction within the reaction channel.

DESCRIPTION OF THE PREFERRED EMBODIMENTS

Figure 1:
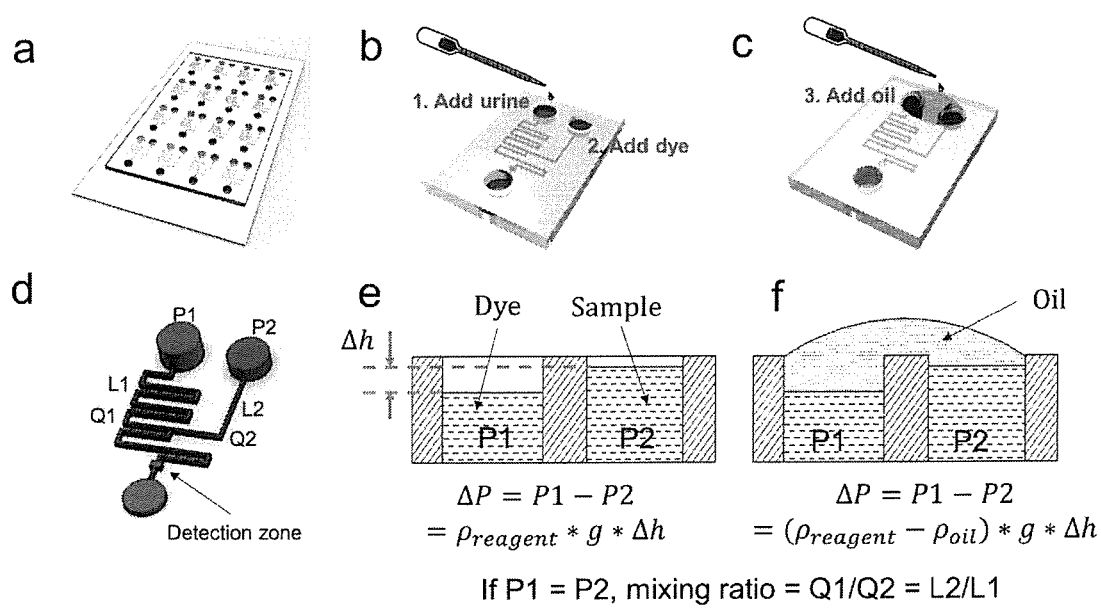
FIG. 1. Illustration of working principle of the UAL-Chip. (a) A complete UAL-Chip with 16 mixing units; (b-c) The operation procedure for single mixing unit; (d) The fluidic network in single mixing unit. P1 and P2 are the hydraulic pressure in the two inlets. L1 and L2 are the lengths of the two branch channels. Q1 and Q2 and the flow rate of the two branch channels; (d-f) Explanation of the pressure-balancing strategy. Ah indicates the liquid height difference between the two inlets, which causes the pressure difference. Adding oil to connect these two inlets balances this pressure difference, making the mixing ratio only dependent on the ratio of lengths of the two branch channels, which is identical for all the 16 units.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Urinary albumin level is an important indicator of kidney damage in chronic kidney disease (CKD) diagnosis but an effective, routine albumin detection tool is lacking.

A microfluidics-based fluorescent test of urinary albumin must be able to precisely control the mixing ratio of the reacting dye and the test sample. One possible solution is to design mechanical structures for on-chip volume metering. However, the main drawback of this approach is the requirement for complex device designs and/or sample manipulation. [4] Alternatively, the mixing ratio can be controlled by continuous mixing of the reacting dye and the test sample driven by pressure flows at defined flow rate ratios. An obvious way is to use two external pumps to control the injection rate of the dye and sample. [5] However, this will increase the cost and complexity of the system. A standalone device that can still maintain a precise mixing ratio is desirable to enable the POC detection of albumin. Furthermore, a method that allows for simple sample preparation without the need of a precise pipette is preferable.

To accomplish these goals, we developed the fluorescent microfluidic urinary albumin chip (UAL-Chip), which exploits the nonimmunological fluorescent assay. In this chip, we constructed a passive and continuous mixing module, in which the loading process requires only an inexpensive dropper, and the signal is stable over time, as discussed below. We applied a pressure-balancing strategy based on the immiscible oil coverage which highly improves the precision in controlling the mixing ratio of sample and dye. The UAL-Chip has achieved an estimated limit of detection (LOD) of 5.2 µg/ml using albumin standards, which is below the 30 µg albumin per ml of urine level considered to be indicative of kidney damage. We also assessed the albumin level in 12 CKD patients' urine samples. As discussed below, the results produced from these samples with the UAL-chip are consistent with the traditional well-plate measurements and clinical results.

According to an aspect of the invention, there is provided a method for mixing two reagents to produce a detectable reaction in a microfluidic chip comprising
  providing a microfluidic chip comprising:
    a first reagent inlet in fluid communication with a first reagent channel, said first reagent channel having a height, a width and a length, said first reagent channel having a first reagent flow rate defined by the height, the width and the length of the first reagent channel;
    a second reagent inlet in fluid communication with a second reagent channel, said second reagent channel having a height, a width and a length, said second reaction channel having a second reagent flow rate defined by the height, the width and the length of the second reagent channel;
    said first reagent channel and said second reagent channel meeting at a junction point, said junction point in fluid communication with a reaction channel, and said reaction channel in fluid communication with an outlet;
  applying a quantity of a first reagent solution to the first reagent inlet;
  applying a quantity of a second reagent solution to the second reagent inlet;
  applying a quantity of oil to the first reagent inlet and the second reagent inlet, said oil having a density slightly lower than a density of the first reagent solution and a density slightly lower than a density of the second reagent solution so that said oil floats on top of the first reagent solution and the second reagent solution;
  said first reagent flowing along the first reagent channel at the first reagent channel flow rate and said second reagent flowing along the second reagent channel at the second reagent channel flow rate until said first reagent and said second reagent begin mixing at the junction point, thereby producing a detectable reaction; and
  detecting the detectable reaction within the reaction channel.

Once the two reagents are added to the inlets, gravity will drive the solutions to flow toward the outlet by virtue of the outlet being empty. Because of the small dimensions of the channels, the flow can last for longer than 1 hour even though the volume added at the inlet(s) is small. This provides continuous and stable mixing. Furthermore, the reagents do not need to be added simultaneously because the signal doesn't decay because of the continuous mixing. That is, the reagents in the two inlets don't need to be added simultaneously but the time gap should be smaller than the time required for one reagent to travel from one inlet to another inlet. Depending on the length of the channel, the time may be a few minutes.

In some embodiments, the flow can reach the junction point in about 2-3 minutes. The flow is continuous until the pressure difference between the inlets and outlet is balanced, but this could take a relatively long period of time, for example, longer than 1 hour, due to the small flow rate in microfluidic channels.

As will be appreciated by one of skill in the art, one of the reagents may be a bodily fluid, such as, for example, urine, serum or saliva, or may be another suitable fluid or solution that is being tested.

As will be appreciated by one of skill in the art, for reagents and samples such as the bodily fluids, most of these have a density that is close to water. For example, the density of urine is typically between 1.002 g/ml and 1.030 g/ml, serum is typically 1.025 g/ml, and saliva is typically around 1.0 g/ml.

As will be appreciated by one of skill in the art, a sample of interest can be diluted to a suitable concentration so as to fall within the detection range.

The detectable reaction may be for example a fluorescent reaction or a colorimetric reaction.

For example, one of the reagents may be the dye reagent from the Albumin Fluorescent Assay Kit™, FITC-dextran, rhodamine, or Texas red.

Other suitable reagents for use as part of a detectable reaction will be readily apparent to one of skill in the art. For example, any suitable reagent used in a commercially available kit for detection of a substrate of interest may be used within the invention. That is, there are a large number of assays known in the art which produce a detectable reaction, all of which can be used in the microfluidic chip of the invention, with the advantage that by adjustment of the flow rates of each channel as discussed herein, reagents for the reaction can be mixed together at the desired ratio without measuring the amount of each reagent applied. Similarly, the conditions under which these reactions can be detected are also well-known in the art and can be used with the device and the method of the invention.

The oil may be for example but by no means limited to silicone oil (density of 0.971 g/ml), mineral oil (density of 0.85 g/ml) or Fluorinet™ oil (density of 1.85 g/ml). Other suitable oils will be readily apparent to one of skill in the art.

In some embodiments of the invention, the first reagent inlet and the second reagent inlet are positioned on the chip such that the first inlet and the second inlet can be covered by a single drop of oil after the first reagent solution and the second reagent solution have been applied to the first reagent inlet and the second reagent inlet respectively. That is, the respective inlets are arranged such that they can be covered by a contiguous drop of oil or a single drop of oil once the reagents have been applied to the inlets, as discussed herein.

In some embodiments of the invention, the first reagent and the second reagent are mixed at unequal amounts. That is, the detectable reaction does not require 1:1 mixing of the two reagents by virtue of the engineered difference in the flow rates, as discussed herein.

As discussed herein, the quantity of the first reagent or the quantity of the second reagent may be an unmeasured quantity. That is, the reagents may be applied without measurement of the amount being applied to the inlets. As will be appreciated by one of skill in the art, this removes a considerable source of variability in reactions as with the device and method of the invention, there are no concerns regarding the accuracy of the amount of reagents used in the reaction.

For example, as discussed herein, each reagent may be applied to their respective inlet as a single drop, which is traditionally considered to be approximately 15 µl to approximately 30 µl.

As will be appreciated by one of skill in the art, in addition to depending on channel dimensions, the flow rate of a given reagent solution will also depend on the fluidic viscosity, which one of skill in the art will understand needs to be taken into account when determining flow rate.

Each of the reagent channels may have a length of between 5 mm to 10 cm.

The reaction channel must be long enough to allow for thorough mixing, which will of course depend on the flow rate, and may have a length between 10 mm to 10 cm. In addition, the reaction channel may be configured so as to promote mixing. For example, the reaction channel may have a "zig zag" configuration, with many turns, so as to promote mixing.

The reaction channel and the reagent channels may have a width of between 50 µm to 1 mm.

As discussed in greater detail below, the mixing ratio can be represented as Q1/Q2=L2/L1, where Q1 and Q2 are the flow rates of the first reaction channel and the second reaction channel respectively, and L2 and L1 are the lengths of the second reaction channel and the first reaction channel, respectively.

For example, in one embodiment, the first reagent is urine and the second reagent is a suitable dye reagent for the detection of albumin.

As discussed herein, these reagents can be combined to detect the presence of albumin in urine. For the detection of albumin with the dye reagent from the Albumin Fluorescent Assay Kit™, the suggested mixing ratio is sample:dye=1:6. In some embodiments, this reaction is detected at 620 nm, although other suitable wavelengths may be used and are within the scope of the invention, as discussed herein In some embodiments, the width and depth of both reagent channels are the same but the length of the urine reagent channel may be 6 times that of the dye reagent channel, for example, 36 mm for the urine channel and 6 mm for the dye channel.

As discussed herein, in use, a single drop of urine and a single drop of the fluorescent dye for detection of albumin may be applied to the first reagent inlet and the second reagent inlet respectively. That is, the reagents may be applied without prior measurement, without applying a measured or metered amount. Despite this, the two reagents will mix at a 6:1 ratio because of the difference in the flow rates between the two reagent channels, or in some embodiments, because of the difference in the lengths of the two reagent channels.

In some embodiments, the width of the reagent channels may be about 60 µm.

In some embodiments, the reaction channel may be about 14 mm long and about 100 µm wide.

It is noted that other suitable dimensions can be readily determined by one of skill in the art using routine experimentation.

As will be appreciated by one of skill in the art, such a method can be used to mix any two reagents that need to be added in unequal amounts. Furthermore, the amount of each reagent being added does not need to be accurately measured or measured at all for the proper reaction to take place, that is, for the reaction to take place at the appropriate ratio.

While the examples above describe the use of two reagent channels, it is important to note that in some embodiments the detectable reaction could be produced by more than two reagent channels, for example, channels for three reagents that meet at a single junction point.

Alternatively, two reagent channels may meet at a first junction point to form a first reaction channel and that first reaction channel may meet a third reagent channel at a second junction point downstream of the first junction point.

Furthermore, as shown in FIG. 1a, one chip may include multiple sets of reagent channels. As discussed below, the embodiment shown in FIG. 1 includes 16 sets of identical channels. As discussed below, this may be used for example to test samples from 16 different individuals or may be used to test samples from 8 different individuals twice etcetera.

Alternatively, a single chip may include different reagent/reaction channel combinations, that is, wherein one set of reaction channels is arranged to carry out a specific detectable reaction while a second set of reaction channels is arranged to carry out a second detectable reaction. As will be appreciated by one of skill in the art, in these embodiments, the sample for each reaction may be the same so that for example a urine sample of an individual could be subjected to two different tests, for example, measurement of albumin levels and measurement of creatinine levels.

Figure 4:
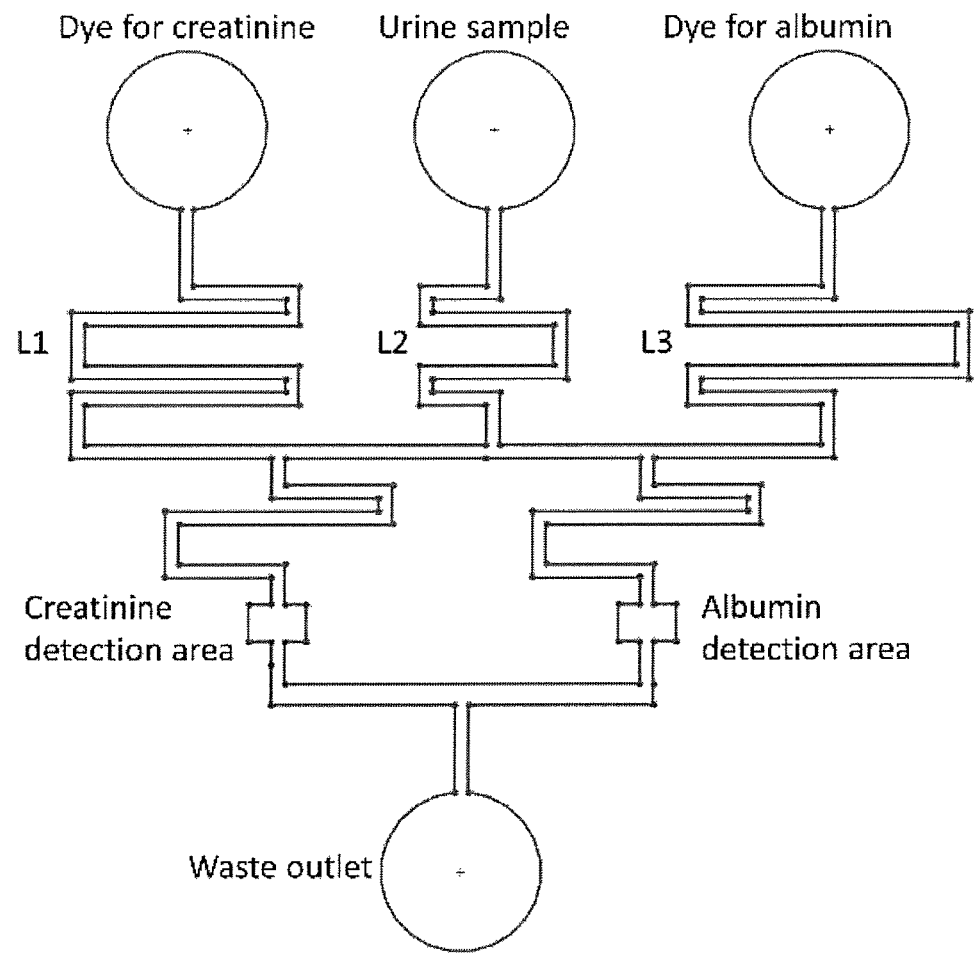
FIG. 4. Schematic diagram of chip arrangement for measurement of both albumin and creatinine from application of a single urine sample.
Figure 5:
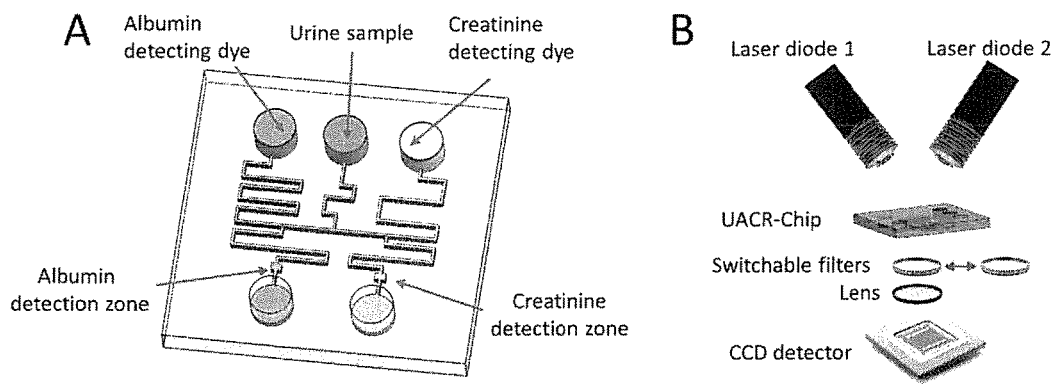
FIG. 5. (A) Illustration of another embodiment of the UACR detection system; (B) schematic diagram of one possible design of the fluorescent imaging system.
Figure 6:
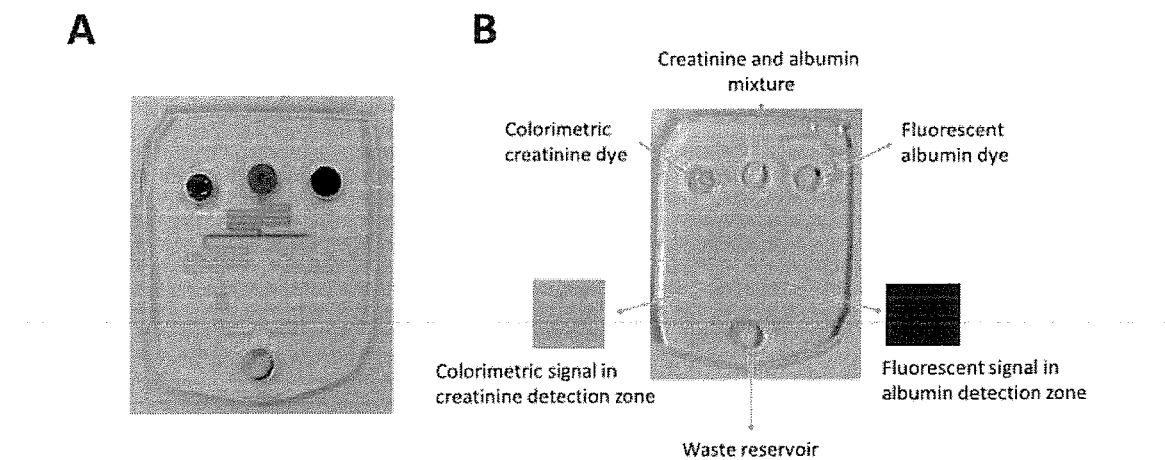
FIG. 6. One embodiment of a microfluidic chip for simultaneous detection of creatinine and albumin. (A) Visualization of the channel pattern in the chip using food dye; (B) The detection of creatinine and albumin standard sample using a colorimetric dye and fluorescent dye. The creatinine detection dye is Infinity™ Creatinine Reagent. The albumin detection dye is albumin blue 580.

Furthermore, shown in FIGS. 4, 5A and 6 are chip designs that can be used to detect urine albumin and creatinine at the same time. As discussed herein, the ratio of L1:L2:L3 or the flow rate of C1:C2:C3 to achieve the desirable mixing ratio between creatinine dye:Urine and Albumin dye:Urine. It is of note that the protocol for use of this device would be similar to the albumin detection, that is, add the dyes and sample to the corresponding inlets, cover all the inlets with the same drop of oil to balance the pressure and detect the fluorescent signals in the detection areas.

In the embodiment shown in FIG. 6, Panel (A) shows the channel pattern in the chip using food dye while Panel (B) shows the detection of creatinine and albumin standard sample using a colorimetric dye and fluorescent dye. In the example shown in FIG. 6, the creatinine detection dye is Infinity™ Creatinine Reagent. The albumin detection dye is albumin blue 580. As can be seen in Panel (B), in this embodiment, the mixture containing creatinine and albumin to be tested is applied to a central inlet. As shown in Panel (A), this mixture, for example, a urine sample, flows along a channel that intersects with channels from the creatinine reporting agent, in this case, a colorimetric creatinine dye, and the albumin reporting agent, in this case, a fluorescent albumin dye. As can be seen in Panel (A), following the intersection point of the respective channels, the sample will mix with the colorimetric creatinine dye and the fluorescent albumin dye respectively. These channels continue to a detection zone which as can be seen in Panels (A) and (B) are of a greater volume than the channel, for easy detection of the colorimetric and fluorescent signal. Accordingly, in some embodiments of the invention, there may be one or more detection zones integrated into the mixing channel that are of a larger volume, for example, wider and/or deeper, than the rest of the channel.

As will be appreciated by one of skill in the art, the ratio of urine to creatinine dye is dependent on the creatinine dye used. While each dye will have its optimum mixing ratio with the sample, determination of this mixing ratio is of course routine experimentation. Once this ratio is known, the lengths of the branch channels can be adjusted accordingly. As can be seen, the chip design is flexible to adjustments to the mixing ratio.

While the albumin dye used herein is albumin blue 580 fluorescent dye, there are other colorimetric dyes for albumin, such as bromocresol green (BCG) and bromocresol purple (BCP). For creatinine, picric acid is a colorimetric dye used in the famous Jaffe reaction. There are other reagents such as metal nanoclusters, whose fluorescent signal will be quenched after reacting with creatinine.

According to another aspect of the invention, there is provided a method for detecting albumin in urine using a microfluidic chip comprising
  providing a microfluidic chip comprising:
    a first reagent inlet in fluid communication with a first reagent channel, said first reagent channel having a height, a width and a length, said first reagent channel having a first reagent flow rate defined by the height, the width and the length of the first reagent channel;
    a second reagent inlet in fluid communication with a second reagent channel, said second reagent channel having a height, a width and a length, said second reaction channel having a second reagent flow rate defined by the height, the width and the length of the second reagent channel;
    said first reagent channel and said second reagent channel meeting at a junction point, said junction point in fluid communication with a reaction channel, and said reaction channel in fluid communication with an outlet;
  applying a quantity of a urine to the first reagent inlet;
  applying a quantity of albumin-detecting dye to the second reagent inlet;
  applying a quantity of oil to the first reagent inlet and the second reagent inlet, said oil having a density slightly lower than a density of the first reagent solution and a density slightly lower than a density of the second reagent solution so that said oil floats on top of the urine and the albumin detecting dye;
  said urine flowing along the first reagent channel at the first reagent channel flow rate and said albumin detecting dye flowing along the second reagent channel at the second reagent channel flow rate until the urine and the albumin detecting dye begin mixing at the junction point, thereby producing a detectable reaction, wherein said first reagent channel flow rate is approximately one sixth of the flow rate of the second reagent channel; and
  detecting the detectable reaction within the reaction channel.

In some embodiments of the invention, the microfluidic chip further comprises a third reagent inlet in fluid communication with a third reagent channel, said third reagent channel having a height, a width and a length, said third reagent channel having a third reagent flow rate defined by the height, the width and the length of the third reagent channel, wherein said first reagent channel and said third reagent channel meet at a second junction point, said junction point in fluid communication with a second reaction channel and said second reaction channel in fluid communication with a second outlet, said second junction point being distal to and separate from the junction point; and the method further comprises applying a creatinine detecting dye to the third inlet; said urine flowing along the first reagent channel at the first reagent channel flow rate and said creatinine detecting dye flowing along the third reagent channel at the third reagent channel flow rate until the urine and the creatinine detecting dye begin mixing at the second junction point, thereby producing a second detectable reaction.

In some embodiments, the first reagent channel is about six times as long as the second reagent channel.

According to another aspect of the invention, there is provided a method for detecting albumin and creatinine in urine using a microfluidic chip comprising
  providing a microfluidic chip comprising:
    a first reagent inlet in fluid communication with a first reagent channel, said first reagent channel having a height, a width and a length, said first reagent channel having a first reagent flow rate defined by the height, the width and the length of the first reagent channel;
    a second reagent inlet in fluid communication with a second reagent channel, said second reagent channel having a height, a width and a length, said second reaction channel having a second reagent flow rate defined by the height, the width and the length of the second reagent channel; and
    a third reagent inlet in fluid communication with a third reagent channel having a height, a width and a length, said third reagent channel having a third reagent flow rate defined by the height, the width and the length of the third reagent channel,
    said first reagent channel and said second reagent channel meeting at a first junction point, said first junction point in fluid communication with a first reaction channel, and said first reaction channel in fluid communication with a first outlet; and
    said first reagent channel and said third reagent channel meeting at a second junction point, said second junction point in fluid communication with a second reaction channel and said second reaction channel in fluid communication with a second outlet, said second junction point being distal to and separate from the first junction point.
  applying a quantity of urine to the first reagent inlet;
  applying a quantity of an albumin-detecting dye to the second reagent inlet;
  applying a quantity of a creatinine-detecting dye to the third reagent inlet;
  applying a quantity of oil to the first reagent inlet and the second reagent inlet, said oil having a density slightly lower than a density of the first reagent solution and a density slightly lower than a density of the second reagent solution so that said oil floats on top of the urine and the albumin detecting reagent;

said urine flowing along the first reagent channel at the first reagent channel flow rate;

said albumin-detecting dye flowing along the second reagent channel at the second reagent channel flow rate and mixing with the urine at the first junction point, thereby producing a first detectable reaction, wherein said first reagent channel flow rate is approximately one sixth of the flow rate of the second reagent channel;

said creatinine detecting dye flowing along the third reagent channel at the third reagent channel flow rate and mixing with the urine, thereby producing a second detectable reaction;

detecting the first detectable reaction to determine albumin concentration; and detecting the second detectable reaction to determine creatinine concentration.

As discussed herein, we have developed a low-cost and high accuracy microfluidic urinary albumin chip (UAL-Chip) for rapid detection of albumin in urine.

There are three major advantages in the design of the UAL-Chip: (1) we incorporated a fluorescent reaction assay into the chip to improve the detection accuracy; (2) we constructed a passive and continuous mixing module in the chip that provides user friendly operation and signal stability; (3) we applied a pressure-balancing strategy based on the use of immiscible oil coverage that achieves precise control of the mixing ratio of sample and dye.

We validated the UAL-Chip using both albumin standards and urine samples from 12 CKD patients and achieved an estimated limit of detection of 8.4 µg/ml which is below the 30 µg/ml level that is indicative of kidney damage. The albumin levels in CKD patients' urine samples measured by UAL-chip is consistent with the traditional well-plate measurements and clinical results, as discussed below.

Specifically, the combination of a passive microfluidic mixer and a pressure-balancing strategy to enable precise chemical mixing for albumin detection has several advantages including: 1) the operation is easy; 2) precise volume metering equipment is not necessary; and 3) the signal is stable over time.

Although this method is based on continuous flow, the consumption of reagent is very small at any given time during the assay due to the low flow rate in the microfluidic device. Specifically, we have verified that 10 µl of sample and reagent could maintain signal stability for more than 1 hour.

The method used in the UAL-Chip demonstrates a general method for the detection of other target markers which require similar mixing strategies between the test sample and a reacting chemical. The mixing ratio can be easily tuned or optimized by changing the length of the branch channels.

As discussed above, shown in FIG. 1 is a UAL-Chip that includes 16 parallel mixing units in a single device but more mixing units could be integrated together to improve the throughput. Additionally, one sample may be run multiple times, thereby providing greater accuracy in the results, as discussed above.

In this study, the signal was read by a fluorescent microscope. However, a portable imaging system can be incorporated to make the system suitable for POC test, such as for example shown in FIG. 5B. This could be achieved using photodiode detector as described in a previous report. [5] Furthermore, using the smartphone to read the fluorescent signal is becoming popular [6] and there are many good examples demonstrating the integration of smartphone and microfluidic technologies for biomedical applications. [7, 8]

Compared with dipstick strips, UAL-Chip shows comparable low-cost (<$1) and fast detection speed (<5 mins) but has lower LOD and better signal stability. The low LOD of 5.2 µg/ml makes this method suitable for diagnosing microalbuminuria and monitoring the progression of kidney disease. The method used in the UAL-Chip could become a general method for the detection of other target markers, which rely on a similar mixing strategy between the test sample and a reagent. As suggested, UACR instead of albumin alone is a better indicator for kidney damage. Development of a chip that can measure both creatinine and albumin is easily achievable given the development of simple fluorescent dyes for creatinine detection.

In some embodiments, passive mixing microstructures may be integrated into the channel to achieve a thorough and rapid mixing in a short mixing channel.

In conclusion, the UAL-Chip represents a portable and disposable microfluidic based tool for determining urinary albumin. The microchip is easy to fabricate at low cost and the operation is simple for end-users.

As will be appreciated by one of skill in the art, the method of the invention may be used to monitor kidney damage, for example, albumin levels in urine, of an individual, as a means of monitoring disease progression.

The method of the invention may also be used for screening at-risk individuals, for example, individuals with a familial history of chronic kidney disease, with diabetes mellitus, high blood pressure or glomerulonephritis.

Individuals diagnosed with chronic kidney disease and who show signs of the disease worsening or anyone who is being monitored regularly and shows signs of the disease worsening may be prescribed medication to reduce blood pressure or may be assigned to a low protein, low salt diet. Such individuals may also be prescribed erythropoietin and/or calcitriol.

Accordingly, some embodiments of the method may be used to monitor kidney damage on an ongoing basis and if the results indicate that the kidney damage is worsening, the patient is assigned a treatment, either a low protein, low salt diet, or medication to reduce blood pressure or specifically prescribed erythropoietin and/or calcitriol.

The invention will now be further explained and elucidated by way of examples; however, the invention is not necessarily limited to or by the examples.

Results

Example 1—Working Principle of the UAL-Chip

In the embodiment shown in FIG. 1a, the UAL-chip has 16 identical mixing units; however, we will discuss one unit to explain the working principle. As illustrated in FIGS. 1b-d, the single mixing unit has two inlets and one outlet. Specifically, each inlet is connected to a channel and the two channels converge upstream of the outlet. The detection zone is located after the two streams converge and proceed along an extended zigzag mixing channel to allow the two input solutions to mix thoroughly. According to the design, the mixing ratio depends on the ratio of volumetric flow rates in the two branches (Q1/Q2). Due to the small dimension of the microfluidic channel, the flow inside the channel is considered as laminar flow. According to Poiseuille's Law, in the case of laminar flow, the volumetric flow rate is given by the pressure difference between the two ends of pipeline divided by the viscous resistance:

$$Q_1 = \frac{P_1 - P_0}{R_1} \quad (1)$$

$$Q_2 = \frac{P_2 - P_0}{R_2} \quad (2)$$

$P_0$ is the pressure at the converging point of the two branches. $R_1$ and $R_2$ are the flow resistances in the two branch channels. $P_1$ and $P_2$ are the pressures in the two input reservoirs. Both the urine and dye solution are water based solutions with very low concentration of solutes, it's reasonable to assume they have the same density $\rho_{reagent}$ and viscosity $\mu$.

$P_1$ and $P_2$ can be estimated using the hydrostatic pressure equation:

$$P_1 = \rho_{reagent} \times g \times h_1 \quad (3)$$

$$P_2 = \rho_{reagent} \times g \times h_2 \quad (4)$$

Where $h_1$ and $h_2$ are the liquid level heights in the two reservoirs.

In one embodiment of the UAL-Chip, the two branches have a rectangular shape with the same width w and height h. The flow resistance $R_1$ and $R_2$ can be expressed as:

$$R_1 \approx \frac{12\mu L_1}{wh^3\left(1 - 0.63 \times \frac{h}{w}\right)} \quad (5)$$

$$R_2 \approx \frac{12\mu L_2}{wh^3\left(1 - 0.63 \times \frac{h}{w}\right)} \quad (6)$$

We can see that $R_1 \propto L_1$ and $R_2 \propto L_2$, where $L_1$ and $L_2$ are the lengths of the branch channels. As will be apparent to one of skill in the art, other arrangements, wherein the width or depth, either alone or in combination with one another and/or the length, are within the scope of the invention.

According to Equation 1-6, if the pressures in the two inlets are same ($P_1 = P_2$), the mixing ratio can be easily calculated using the following equation:

$$\text{Mixing ratio} = \frac{Q_1}{Q_2} = \frac{R_2}{R_1} = \frac{L_2}{L_1} \quad (7)$$

In UAL-Chip, all the 16 units have the identical design, so the $L_2/L_1$ is constant. As long as each unit can meet the requirement of $P_1 = P_2$, all the 16 units will obtain the same mixing ratio. On the other hand, if $P_1$ is not equal to $P_2$, the mixing ratio will be variable, which is proportional to the pressure difference $\Delta P = P_1 - P_2$. So the critical issue becomes how to make the $\Delta P$ as small as possible.

According to Equation 3-4, $P_1$ and $P_2$ are dependent on the liquid levels $h_1$ and $h_2$ in the two reservoirs. However, in the actual experiment, it's difficult to make $h_1 = h_2$ because of variations in the loading volumes and dimensions of the reservoirs. To address this issue, we used a pressure balancing strategy by covering and connecting the two inlets with oil. We chose the oil which is immiscible with the reagents and whose density is a little bit smaller than the reagent; so the oil won't mix with the reagent and will float on the top. The principle of the pressure balancing is illustrated in FIG. 1c-f.

Before adding the oil, the pressure difference between the two inlets is $$\Delta P = P_1 - P_2 = P_{reagent} \times g \times \Delta h \quad (8)$$

After adding the oil on the top and connecting the two inlets, the pressure difference becomes $$\Delta P = P_1 - P_2 = (\rho_{reagent} - \rho_{oil}) \times g \times \Delta h \quad (9)$$

If the density of the oil is very close to the density of the reagent, the $\rho_{reagent} - \rho_{oil}$ becomes very small and thus the pressure difference $\Delta P$ becomes negligible. To give an example, we assume the height difference between the two loading ports is 1 mm; the density of the reagent and oil is 1 g/cm$^3$ and 0.963 g/cm$^3$, respectively. The pressure difference $\Delta P$ between the two ports will be 10 Pa before balancing and 0.37 Pa after balancing. The difference could be further decreased if we use an oil that has a density closer to the reagent.

Figure 2:
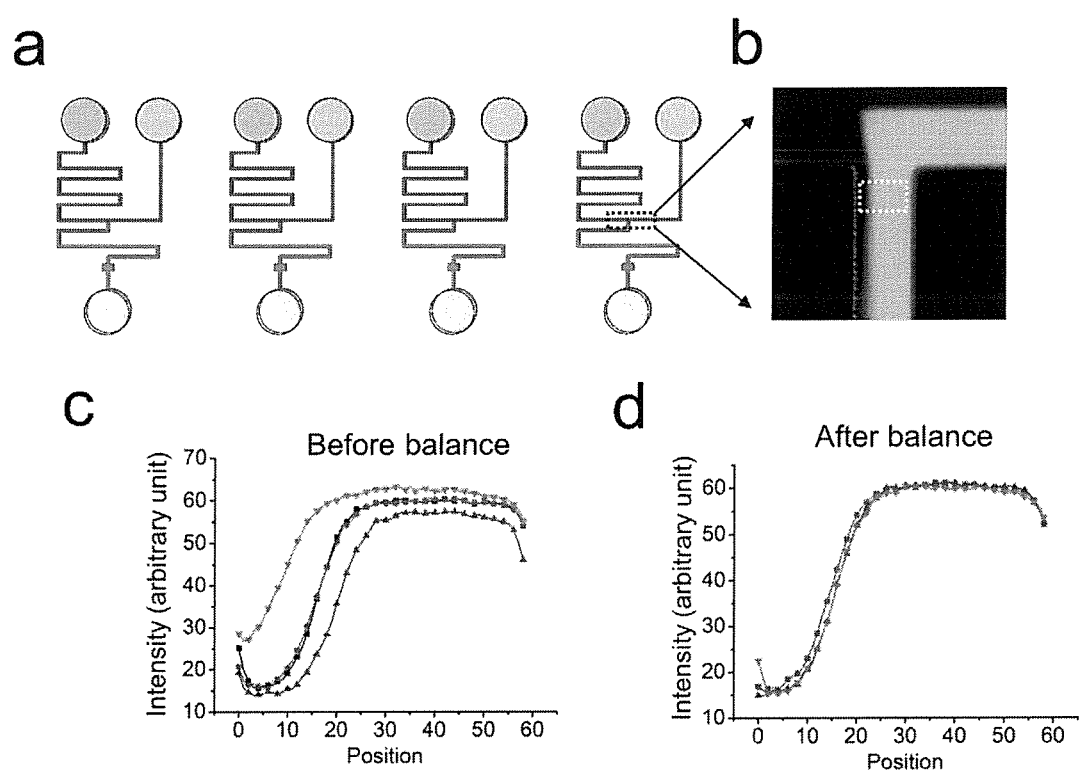
FIG. 2. Validation of pressure-balancing strategy. (a) Four identical mixing units were used to perform this test; (b) the fluorescent image just after the converging area. The white dash box indicates the place used to plot the intensity profile; (c) The intensity profile in the four channels before pressure-balancing; (d) The intensity profile in the four channels after pressure-balancing.

To validate this method, we fabricated a device with 16 parallel mixing units and we used 4 of them to test the flow-balancing strategy (FIG. 2a). We added FITC-dextran dye and water into the two inlets respectively. Then we measured the fluorescent profile in the area just after the two streams converged (FIG. 2b). The duty ratio in the profile can be used to indirectly represent the mixing ratio of the dye and water. In this experiment, we loaded different volumes in the four units on purpose to make the pressures imbalanced. As shown in FIG. 2c, the intensity profiles in the four units are quite different. After we added oil to cover the inlets, the intensity profiles become almost identical (FIG. 2d), suggesting that the pressures are balanced and thus the mixing ratio became identical in all the four mixing units.

To summarize, the UAL-Chip is easy to operate by using passive pumping method to infuse the reagents. The oil based pressure balancing strategy can significantly decrease the variation of mixing ratios between different mixing units, thus improving the detection accuracy of the fluorescent assay.

Example 2—Validation of the UAL-Chip Using the Albumin Standard

Figure 3:
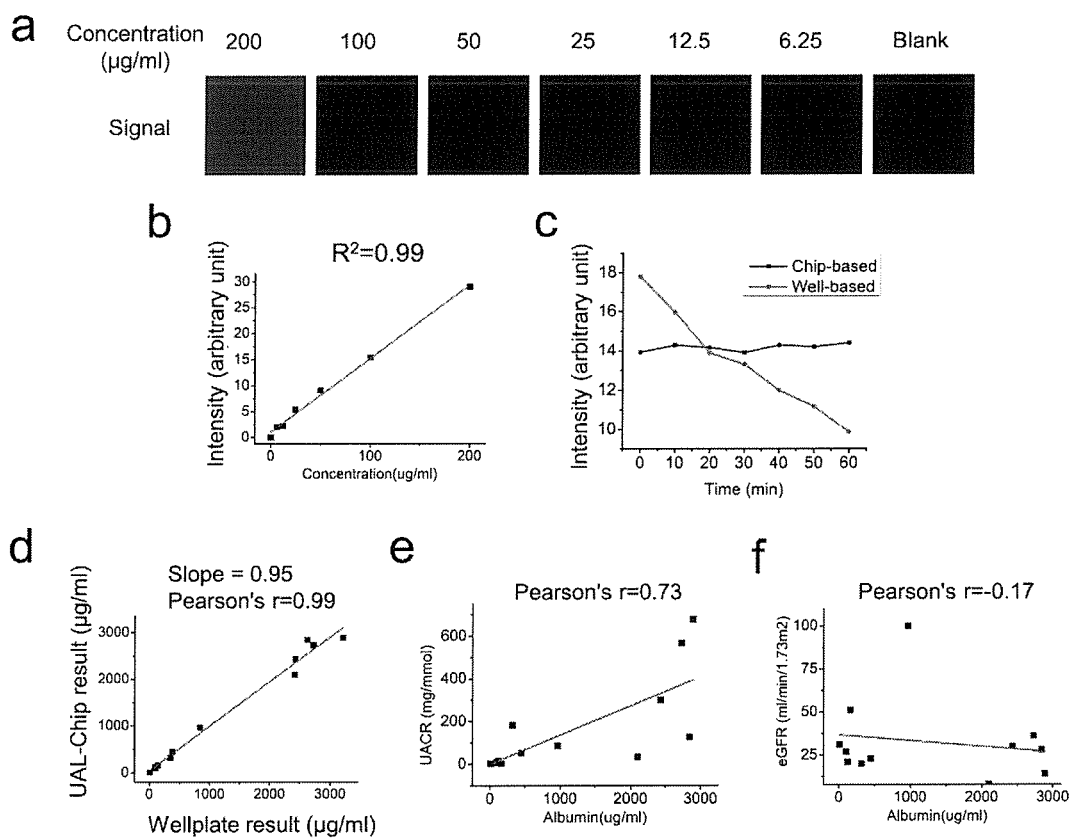
FIG. 3. Validation of UAL-Chip using albumin standards and CKD urine samples. (a) The fluorescent signals depending on the albumin concentrations; (b) The calibration curve of the intensity against the albumin standard concentration. The solid line is the linear fit of the data (R2=0.99); (c) Photostability test between UAL-Chip and well-plate; (d) Comparison between the UAL-Chip measurements and well-plate measurements (Pearson correlation coefficient=0.99; slope=0.95); (e) Positive correlation between albumin level and UACR value (Pearson correlation coefficient=0.73); (f) No correlation is found between albumin level and eGFR value (Pearson correlation coefficient=−0.17).

To get the calibration curve for the albumin detection, an HSA standard was serially diluted to different concentrations (200, 100, 50, 25, 12.5, 6.25 µg/ml and blank). The fluorescent signal was captured after loading the standard HSA and dye solution to the different mixing units of the microfluidic chip (FIG. 3a). The calibration curve was plotted after subtracting the blank signal (FIG. 3b). The $R^2$ value of the linear fit is 0.99. The LOD calculated from regression line is 5.2 µg/ml, which is >3 times lower than the normal range (clinical cut-off level: ~20 µg/ml).

Compared to the traditional well-plate method, UAL-Chip also showed great advantage in signal stability due to its continuous mixing property. In the well-plate method, the sample and dye signal is premixed and loaded into a well. The fluorescent signal decays slowly due to concentration changes caused by solvent evaporation. In the UAL-Chip, fresh reagents flow into the detection zone continuously; the sealed channel and the oil that covers the reagent wells prevent evaporation as well. As illustrated in FIG. 3c, the signal of the UAL-Chip maintained stable in the one-hour stability test while the signal using well-plate decayed significantly. The standard deviation of the signal intensity in one hour is 0.64 for the UAL-Chip and 8.11 for the well-plate method. This indicates that the signal decays about 48% after 1 hour in well-plate.

The UAL-Chip demonstrates a linear relationship between concentration and fluorescent intensity in 0-200 µg/ml HSA standards and the LOD is below the normal range of albumin level in urine. In addition, the significant signal stability of the UAL-Chip decreases detection inaccuracy caused by variations in measurement time points.

As will be appreciated by one of skill in the art, using the conventional test, the signal can decay by almost 50% within one hour whereas using the method described herein, the signal is stable for over an hour. This decay in the prior art is significant because a signal that is read too late may miss an individual who has albumin levels of 30-40 µg/ml (which is an indication of kidney disease).

Example 3—Validation of the UAL-Chip Using CKD Samples

The developed method was further validated using real clinical urine samples from patients who have been diagnosed with CKD. The collected patient information includes disease stage, gender, and some biomarker measurements such as eGFR, UACR, serum creatinine and albumin, HgA1C and low density lipoprotein (LDL). We measured the albumin concentration in the urine samples from 12 CKD patients using the UAL-Chip and the well-plated method. Because the dynamic range of the albumin concentration is large, a series of dilutions of the urine samples were prepared and measured. The concentrations were calculated based on the calibration curve. The albumin test results using the microfluidic mixer were in agreement with the traditional well-plate-based method (FIG. 3d). The Pearson correlation coefficient of these two measurements is 0.99.

We further compared the albumin results measured by the UAL-Chip with the clinical results (measured by Roche Cobas c501 using an immunoturbidimetric assay). Although clear positive correlation was observed between these two measurements (the Pearson correlation coefficient is 0.73; FIG. 3e), they are not in perfect agreement, especially for the samples that have high albumin levels. There are several reasons for these differences. First, the tests were performed on different samples collected on different dates. Urinary albumin excretion rates in CKD vary significantly from day to day, diminishing the correlation between samples collected on different days. Moreover, this variability is higher at higher levels of albumin excretion. In addition, the multiple dilutions required to fit the measurement into the linear range of the calibration curve will have further weakened correlation at high albumin levels.

We then used the recommended cutoffs of the urine albumin levels for albuminuria (normal: <20 µg/ml; microalbuminuria: 20-200 µg/ml; clinical albuminuria: >200 µg/ml) [5] to classify the patients into different groups and compared the classification accuracy between the UAL-Chip results and clinical albumin results (Table 1). Only two patients were misclassified in the normal group and the microalbuminuria group. The classification accuracy was 10/12=83%.

In clinical practice, UACR instead of albumin alone is considered a better indicator of kidney damage as it can control for variations in urine concentration. [4] Three albuminuria categories (A1: UACR $\leq$3 mg/mmol, normal to mildly increased; A2: UACR 3-30 mg/mmol, moderately increased; A3: UACR >30 mg/mmol, severely increased) are usually employed to indicate the kidney damage levels. [4] To evaluate the sensitivity, specificity, and positive and negative predictive values of using the albumin levels by the UAL-Chip results to determine albuminuria, we used cross-tabulation tables for pairs of albumin positivity level $\geq$20 µg/ml (or $\geq$200 µg/ml) and the reference standard of an UACR$\geq$3 mg/mmol (or $\geq$30 mg/mmol). The accuracy values are as shown in Table 2. The sensitivity, specificity, PPV, NPV, and accuracy of the UAL-Chip results are 100% for both the detection of UACR$\geq$3 mg/mmol and UACR$\geq$30 mg/mmol from the test results of 12 patients.

Although the sample size of 12 patients is relatively small, these results at least in part suggest that UAL-Chip is reliable in testing clinical urine samples and its measurement is comparable with traditional methods for measurement in a clinical setting.

Clinical test usually measure the UACR instead of albumin level to control for variations in urine flow rate. Although UACR is a normalized ratio, the changes in albumin excretion will reflect change in the ratio. Indeed, clear positive correlation was observed between albumin concentration and UACR (FIG. 3e). The Pearson correlation coefficient is 0.73. We also compared the albumin level to the eGFR value. However, no correlation relationship is observed (FIG. 3f). This is reasonable considering that eGFR and UACR are two independent markers for renal assessment and no direct association has been reported between them. These results suggest that UAL-Chip is reliable in testing clinical urine samples and its measurement is comparable with the traditional method and measurement in a clinical setting.

Example 4—Comparison of the UAL-Chip with the Dipstick Strips and Other Laboratory Methods Table 3 shows the comparison of our method with some widely-used dipstick strips and laboratory methods. Compared with the immunologically-based and HPLC-based laboratory methods, our method has higher LOD but much lower cost. Compared with dipstick methods, our chip has comparable costs and detection speed but lower LOD, which can distinguish the microalbuminuria from normal level (cutoff of 20 mg/L). In addition, the signal stability of our method is much better, reducing the potential for measurement error.

Methods

Microfluidic Device Design and Fabrication

The device pattern was designed using AUTOCAD and printed on a transparent film with high resolution. A SU-8 device master was fabricated on a 3-inch silicon wafer using photolithography process. Polydimethylsiloxane (PDMS) replica devices were made from the SU-8 master mold. 3 mm diameter holes were punched in the PDMS slab as the inlet and outlet reservoirs. The PDMS slab was bonded to a glass slide to seal the channel.

Clinical Samples and Reagents

The urine samples from CKD patients were collected at the Seven Oaks General Hospital through an approved ethical protocol. The clinical descriptors of the patients were documented by the hospital (See SI for the information). The Albumin Blue Fluorescent Assay Kit (Active Motif, 15002) was used to measure albumin levels in urine. The silicone oil (Alfa Aesar, A1272822) was used to cover and connect the solution loading ports to balance the pressure.

Albumin Detection Assay

The dye reagent and standard human serum albumin (HSA) was prepared according to the product datasheet. Raw urine samples or diluted urine samples by DPBS were used as the test samples. The operation procedure was illustrated in FIG. 1a. The dye solution and test samples were added to the corresponding inlets in the microfluidic device using a dropper. The two inlets were then covered and connected by adding one drop of the oil on the top. Wait for 2-3 minutes until the reagents enter the detection zone. The fluorescent signal was recorded by an inverted fluorescent microscope. The signals of standard HSA were used to construct the calibration curve. The concentrations of the unknown samples were calculated according to the calibration curve. The LOD is calculated from the regression line of the calibration curve (3*standard error of regression/slope). Each test has two repeats. We also tested the albumin level using the well-plate method as the control. The sample and dye were loaded and mixed in the wells using a pipette at a fixed ratio. The signal was recorded by a multi-plate reader (Synergy 4 HT). Each test sample was assayed in duplicate.

Photostability Test

The stability of the of the fluorescence intensity was compared between the microfluidic method and well-plate method. In the microfluidic device, the sample and dye were loaded into the inlets and covered by oil. In the well-plate, the sample and dye were loaded into a well and mixed thoroughly using the pipette. The fluorescence emission was imaged by fluorescent time-lapse imaging for 1 hour with an interval of 3 minute. The intensity versus time plots were used to evaluate the photostability.

While the preferred embodiments of the invention have been described above, it will be recognized and understood that various modifications may be made therein, and the appended claims are intended to cover all such modifications which may fall within the spirit and scope of the invention.

TABLE 1

Classification accuracy according to the albumin levels from the UAL-Chip results and the clinical results (Cobas c501, immunoturbidimetry). The numbers in the table indicate different patients (totally 12 patients).

| Albumin level (μg/ml) | UAL-Chip | Clinical test |
| --- | --- | --- |
| Normal (<20) | 2 | 7 |
| Microalbuminuria (20-200) | 4, 7, 8 | 2, 4, 8 |
| Clinical albuminuria (>200) | 1, 3, 5, 6, 9, 10, 11, 12 | 1, 3, 5, 6, 9, 10, 11, 12 |

TABLE 2

Diagnostic accuracy of the UAL-Chip results for detections of UACR ≥3 mg/mmol and UACR ≥3 mg/mmol (from total 12 patients).

| | Sensitivity | Specificity | PPV | NPV | Accuracy |
| --- | --- | --- | --- | --- | --- |
| Albumin ≥ 20 μg/ml (UAL-Chip) for detection of UACR ≥3 mg/mmol | 100% | 100% | 100% | 100% | 100% |
| Albumin ≥ 200 μg/ml (UAL-Chip) for detection of UACR ≥30 mg/mmol | 100% | 100% | 100% | 100% | 100% |

TABLE 3

Comparison of the UAL-Chip with the dipstick strips and other laboratory methods. Most of the data is from the manual books of each product. The data of radioimmunoassay and HPLC method is from ref [9].

| | Assays | LOD for albumin | Detection peeds | Cost | Signal stability |
| --- | --- | --- | --- | --- | --- |
| Dipstick strips | Multistix 10 SG | 150 mg/L | Fast (<5 minutes) | $0.48/strip | Poor (<2 mins) |
| | Chemstrip | 60 mg/L | Fast (<5 minutes) | $0.65/strip | Poor (<2 mins) |
| | Clinitek Microalbumin | 30 mg/L | Fast (<5 minutes) | $4/strip | Poor (<2 mins) |
| | Micral-Test strip | 20 mg/L | Fast (<5 minutes) | $10/strip | Poor (<5 mins) |
| Immunologically-based laboratory methods | Immunonephelometry (Beckman Array Analyzer) | 2 mg/L | Fair (10 minutes) | High (high-cost reagents and equipment requirement) | ND |
| | Immunoturbidimetry (Cobas c501) | 3 mg/L | Fair (10 minutes) | | ND |
| | Radioimmunoassay | 16 μg/L | Extremely slow (3-4 days) | | ND |
| HPLC laboratory method | | 2 mg/L | Slow (10-60 minutes) | | ND |
| UAL-Chip | | 5.2 mg/L | Fast (<5 minutes) | $0.16/test (include the cost of device and reagent) | Good (>1 hr) |

ND: not determined.

REFERENCES

[1] Jha, V.; Garcia-Garcia, G.; Iseki, K.; Li, Z.; Naicker, S.; Plattner, B.; Saran, R.; Wang, A. Y.-M.; Yang, C.-W., Lancet 2013, 382 (9888), 260-272. DOI http://dx.doi.org/10.1016/S0140-6736(13)60687-X.

[2] Tonelli, M.; Muntner, P.; Lloyd, A.; Manns, B. J.; James, M. T.; Klarenbach, S.; Quinn, R. R.; Wiebe, N.; Hemmelgarn, B. R., Annals of internal medicine 2011, 154 (1), 12-21.

[3] Busby, D. E.; Bakris, G. L., The Journal of Clinical Hypertension 2004, 6 (s11), 8-12.

[4] Du, W.; Li, L.; Nichols, K. P.; Ismagilov, R. F., Lab on a Chip 2009, 9 (16), 2286-2292.

[5] Hofmann, O.; Wang, X.; Bradley, D. D., Lab on a Chip 2005, 5 (8), 863-868.

[6] Coskun, A. F.; Nagi, R.; Sadeghi, K.; Phillips, S.; Ozcan, A., Lab on a Chip 2013, 13 (21), 4231-4238.

[7] Yang, K.; Wu, J.; Peretz-Soroka, H.; Zhu, L.; Li, Z.; Sang, Y.; Hipolito, J.; Zhang, M.; Santos, S.; Hillier, C., Biosensors and Bioelectronics 2018, 99, 259-267.

[8] Yang, K.; Peretz-Soroka, H.; Liu, Y.; Lin, F., Lab on a Chip 2016, 16 (6), 943-958.

The invention claimed is:

1. A method for mixing two reagents to produce a detectable reaction in a microfluidic chip comprising:
    providing a microfluidic chip comprising:
        a first reagent inlet at a top surface of the microfluidic chip in fluid communication with a first reagent channel, said first reagent channel having a height, a width and a length, said first reagent channel having a first reagent flow rate defined by the height, the width and the length of the first reagent channel;
        a second reagent inlet at a top surface of the microfluidic chip in fluid communication with a second reagent channel, said second reagent channel having a height, a width and a length, said second reaction channel having a second reagent flow rate defined by the height, the width and the length of the second reagent channel;
        said first reagent channel and said second reagent channel meeting at a junction point, said junction point in fluid communication with a reaction channel, and said reaction channel in fluid communication with an outlet;
    applying a quantity of a first reagent solution to the first reagent inlet;
    applying a quantity of a second reagent solution to the second reagent inlet;
    applying a drop of oil covering and connecting both the first reagent inlet and the second reagent inlet, said oil having a density slightly lower than a density of the first reagent solution and a density slightly lower than a density of the second reagent solution, wherein said oil floats on top of the first reagent solution in the first reagent inlet and the second reagent solution in the second reagent inlet, thereby balancing a first pressure of the first reagent inlet with a second pressure of the second reagent inlet such that a mixing ratio of the first reagent solution and the second reagent solution is determined based on the length of the first reagent channel and the length of the second reagent channel;
    said first reagent solution flowing along the first reagent channel at the first reagent channel flow rate and said second reagent solution flowing along the second reagent channel at the second reagent channel flow rate and mixing at the junction point, thereby producing a detectable reaction; and detecting the detectable reaction within the reaction channel.

2. The method according to claim 1 wherein the oil is silicone oil or mineral oil.

3. The method according to claim 1 wherein the first reagent inlet and the second reagent inlet are positioned on the microfluidic chip such that the first reagent inlet and the second reagent inlet can be covered by the drop of oil after the first reagent solution and the second reagent solution have been applied to the first reagent inlet and the second reagent inlet respectively.

4. The method according to claim 1 wherein the first reagent solution and the second reagent solution are mixed at unequal amounts.

5. The method according to claim 1 wherein the first reagent solution and the second reagent solution mix at a mixing ratio represented as Q1/Q2, where Q1 is the first reaction channel flow rate and Q2 is the second reaction channel flow rate, and wherein Q1/Q2 is not equal to 1.

6. The method according to claim 1 wherein the first reagent solution is urine.

7. The method according to claim 1 wherein the second reagent is a dye for detection of albumin.

8. The method according to claim 1 wherein the first reagent solution is a bodily fluid.

9. The method according to claim 8 wherein the bodily fluid is urine, serum or saliva.

10. The method according to claim 1 wherein at least one the first reagent solution and the second reagent solution is applied to the microfluidic chip as a reagent drop.

11. The method according to claim 10 wherein the reagent drop is an unmeasured drop.

12. The method according to claim 11 wherein the first reagent channel is about six times as long as the second reagent channel.

13. A method for detecting albumin in urine using a microfluidic chip comprising:
    providing a microfluidic chip comprising:
        a first reagent inlet at a top surface of the microfluidic chip in fluid communication with a first reagent channel, said first reagent channel having a height, a width and a length, said first reagent channel having a first reagent flow rate defined by the height, the width and the length of the first reagent channel;
        a second reagent inlet at a top surface of the microfluidic chip in fluid communication with a second reagent channel, said second reagent channel having a height, a width and a length, said second reaction channel having a second reagent flow rate defined by the height, the width and the length of the second reagent channel;
        said first reagent channel and said second reagent channel meeting at a junction point, said junction point in fluid communication with a reaction channel, and said reaction channel in fluid communication with an outlet;
    applying a quantity of urine to the first reagent inlet;
    applying a quantity of an albumin-detecting dye to the second reagent inlet;
    applying a drop of oil covering and connecting both the first reagent inlet and the second reagent inlet, said oil having a density slightly lower than a density of the first reagent solution and a density slightly lower than a density of the second reagent solution, wherein said oil floats on top of the urine in the first reagent inlet and the albumin detecting reagent in the second reagent inlet, thereby balancing a first pressure of the first reagent inlet with a second pressure of the second reagent inlet such that a mixing ratio of the first reagent solution and the second reagent solution is determined based on the length of the first reagent channel and the length of the second reagent channel;

said urine flowing along the first reagent channel at the first reagent channel flow rate and said second reagent flowing along the second reagent channel at the second reagent channel flow rate, wherein said first reagent channel flow rate is approximately one sixth of the flow rate of the second reagent channel; the urine and the albumin-detecting dye mixing at the junction point, thereby producing a detectable reaction, and detecting the detectable reaction within the reaction channel to determine albumin concentration.

14. The method according to claim 13 wherein the oil is silicone oil or mineral oil.

15. The method according to claim 13 wherein the first reagent inlet and the second reagent inlet are positioned on the chip such that the first inlet and the second inlet can be covered by the drop of oil after the urine has been applied to the first reagent inlet and the albumin-detecting dye has been applied to the second reagent inlet.

16. The method according to claim 13 wherein the microfluidic chip further comprises a third reagent inlet in fluid communication with a third reagent channel having a height, a width and a length, said third reagent channel having a third reagent flow rate defined by the height, the width and the length of the third reagent channel, wherein said first reagent channel and said third reagent channel meet at a second junction point, said second junction point in fluid communication with a second reaction channel and said second reaction channel in fluid communication with a second outlet, said second junction point being distal to and separate from the junction point.

17. The method according to claim 16 further comprising applying a quantity of creatinine-detecting dye to the third reagent inlet, said creatinine detecting dye flowing along the third reagent channel at the third reagent channel flow rate and mixing with the urine at the second junction point, thereby producing a second detectable reaction; and detecting the second detectable reaction to determine creatinine concentration.

18. A method for detecting albumin and creatinine in urine using a microfluidic chip comprising:
providing a microfluidic chip comprising:
a first reagent inlet at a top surface of the microfluidic chip in fluid communication with a first reagent channel, said first reagent channel having a height, a width and a length, said first reagent channel having a first reagent flow rate defined by the height, the width and the length of the first reagent channel;
a second reagent inlet at a top surface of the microfluidic chip in fluid communication with a second reagent channel, said second reagent channel having a height, a width and a length, said second reaction channel having a second reagent flow rate defined by the height, the width and the length of the second reagent channel; and
a third reagent inlet in fluid communication with a third reagent channel having a height, a width and a length, said third reagent channel having a third reagent flow rate defined by the height, the width and the length of the third reagent channel,
said first reagent channel and said second reagent channel meeting at a first junction point, said first junction point in fluid communication with a first reaction channel, and said first reaction channel in fluid communication with a first outlet; and
said first reagent channel and said third reagent channel meeting at a second junction point, said second junction point in fluid communication with a second reaction channel and said second reaction channel in fluid communication with a second outlet, said second junction point being distal to and separate from the first junction point;
applying a quantity of urine to the first reagent inlet;
applying a quantity of an albumin-detecting dye to the second reagent inlet;
applying a quantity of a creatinine-detecting dye to the third reagent inlet;
applying a drop of oil covering and connecting both the first reagent inlet and the second reagent inlet, said oil having a density slightly lower than a density of the first reagent solution and a density slightly lower than a density of the second reagent solution, wherein said oil floats on top of the urine and the albumin detecting reagent, thereby balancing a first pressure of the first reagent inlet with a second pressure of the second reagent inlet such that a mixing ratio of the first reagent solution and the second reagent solution is determined based on the length of the first reagent channel and the length of the second reagent channel;
said urine flowing along the first reagent channel at the first reagent channel flow rate; said albumin-detecting dye flowing along the second reagent channel at the second reagent channel flow rate and mixing with the urine at the first junction point, thereby producing a first detectable reaction, wherein said first reagent channel flow rate is approximately one sixth of the flow rate of the second reagent channel;
said creatinine detecting dye flowing along the third reagent channel at the third reagent channel flow rate and mixing with the urine, thereby producing a second detectable reaction;
detecting the first detectable reaction to determine albumin concentration; and
detecting the second detectable reaction to determine creatinine concentration.

19. The method according to claim 18 wherein the oil is silicone oil or mineral oil.

20. The method according to claim 18 wherein the first reagent inlet and the second reagent inlet are positioned on the microfluidic chip such that the first reagent inlet and the second reagent inlet can be covered by the drop of oil after the first reagent solution and the second reagent solution have been applied to the first reagent inlet and the second reagent inlet respectively.

21. The method according to claim 18 wherein at least one the first reagent and the second reagent is applied to the microfluidic chip as a reagent drop.

22. The method according to claim 21 wherein the reagent drop is an unmeasured drop.

* * * * *